United States Patent [19]

Fried et al.

[11] Patent Number: 5,066,829
[45] Date of Patent: Nov. 19, 1991

[54] PREPARATION OF CARBOXYLIC ACID ESTERS

[75] Inventors: Herbert E. Fried; Thomas H. Johnson, both of Houston, Tex.

[73] Assignee: Shell Oil Company, Houston, Tex.

[21] Appl. No.: 510,309

[22] Filed: Apr. 17, 1990

[51] Int. Cl.$^5$ ............................................. C07C 67/02
[52] U.S. Cl. .................................................... 560/217
[58] Field of Search ......................................... 560/217

[56] References Cited

U.S. PATENT DOCUMENTS

| | | | |
|---|---|---|---|
| 2,093,695 | 9/1937 | Larson | 260/106 |
| 3,534,087 | 10/1970 | Leftin et al. | 260/491 |
| 3,641,120 | 2/1972 | Broderick et al. | 260/491 |
| 3,755,386 | 8/1973 | Wilke et al. | 260/410.9 |
| 3,783,136 | 1/1974 | Inukai et al. | 260/410.9 |
| 3,855,255 | 12/1974 | Dohr et al. | 260/410.9 |
| 4,506,095 | 3/1985 | Koermer | 560/205 |
| 4,623,748 | 11/1986 | Johnson | 560/204 |

FOREIGN PATENT DOCUMENTS

| | | |
|---|---|---|
| 0739208-Q | 9/1968 | Belgium . |
| 2044159-Q | 9/1970 | Fed. Rep. of Germany . |
| 2063515 | 7/1971 | Fed. Rep. of Germany . |
| 3149-979 | 12/1980 | Fed. Rep. of Germany . |
| 496265 | 3/1978 | U.S.S.R. . |
| 8100-846 | 9/1979 | World Int. Prop. O. . |

OTHER PUBLICATIONS

Thermal Addition of Monoolefins to Dienophiles, Albisetti et al., Jun. 5, 1956, 2637–2641.
Eutectic Potassium-Sodium-Aluminum Chloride as a Mild Catalyst for Ene Reactions: Simple Synthesis of the Sex Pheromone from Douglas Fir Tussock Moth; J. Org. Chem., vol. 43, No. 22, 1978; Mar. 13, 1978, 4387 and 4388.
The Lewis Acid Catalysis of Ene Reactions, Snider; J. Org. Chem., vol. 39, No. 2, 1974; 255 and 256.

*Primary Examiner*—Paul J. Killos
*Attorney, Agent, or Firm*—Pamela J. McCollough

[57] ABSTRACT

A process for the preparation of higher alkyl acrylic acid esters which comprises the addition reaction of olefins to alkyl acrylic acid esters catalyzed by tantalum pentachloride.

7 Claims, No Drawings

PREPARATION OF CARBOXYLIC ACID ESTERS

This invention relates to a process for the preparation of carboxylic acid esters, which are known to find use, for example, in formulating medicines, ointments, cosmetics and lubricating oils, as soaps, as plasticizers, as solvents and as chemical intermediates. More particularly, this invention relates to a reaction process for the preparation of higher alkyl acrylic acid esters, in which olefins are contacted and reacted with lower alkyl acrylic acid esters, in the presence of a tantalum pentachloride catalyst.

Various catalysts are known to promote the "ene reaction" of olefins with alpha-, beta-unsaturated carboxylic acid esters for the production of unsaturated carboxylic acid esters. For instance, U.S. Pat. No. 3,783,136 and German Offenlegungsschrift 2063515 both describe the use of $AlCl_3$ and $AlBr_3$ as catalysts for such reactions. U.S. Pat. No. 4,506,095 describes the reaction of linear alpha-olefins with alkyl acrylates catalyzed by an organometallic catalyst of the formula $R_n$—Al—$X_{3-n}$, wherein R is an organic radical containing between about 1 and 12 carbon atoms, n is the integer 1 or 2, and X is chlorine or bromine. U.S. Pat. No. 3,641,120 describes the reaction of an ester with an olefin in the presence of a combination of a manganic carboxylic acid salt or oxide with a zirconyl carboxylic acid salt or zirconium oxide. The publication by B. R. Snider in J. Org. Chem., vol. 39, no. 2 (1974), p. 255, refers generally to Lewis acid catalysts for ene reactions, but illustrates only the use of aluminum chloride and zinc bromide. U.S. Pat. No. 3,855,255 describes the reaction of carboxylic acid esters by reacting diolefins with methacrylate esters in the presence of an organometallic complex of zero-valent nickel and an electron donor. U.S. Pat. No. 2,093,695 discloses preparation of carboxylic acid esters by reaction of acyloxy compounds with olefinic hydrocarbons catalyzed by activated charcoal, inorganic acids, the halogens and various halides of calcium, boron, cadmium, zinc, calcium and potassium. Akermark et al (J. Org. Chem., vol. 43, no. 22 (1978), p. 4387) have reported that the eutectic mixture of $AlCl_3$, NaCl, and KCl is a superior ene reaction catalyst. U.S. Pat. No. 3,892,788 teaches a ligand-stabilized Pt(II) dihalide complex combined with a Group IVb metal halide as a catalyst for such reactions. South African patent 496,265 describes one such reaction catalyzed by various organo-metal compounds. According to German Offenlegungsschrift 2044159, a reaction between acrylic acid esters and dienes is catalyzed by an organometallic complex of zero-valent iron and a triaryl compound of an element of Group V. U.S. Pat. Nos. 3,755,386 and 4,144,257 and Belgian published application 739,208 describe similar reactions using complexes of Group VIII compounds, as well as various compounds and complexes of iron, nickel or cobalt. U.S. Pat. Nos. 4,009,203 and 3,534,087, German Offenlegungsschrift 3149979 and World Patent No. 8100846 describe related reactions of acids and olefins catalyzed by an acyloxy-stannic trihalide or a perfluorosulfonic acid resin or a crystalline metal silicate or an aluminum silicate containing a Group VIII metal compound and a polyvalent metal halide.

SUMMARY OF THE INVENTION

It has now been found that the reaction of alkyl esters of acrylic acid with olefins is promoted by a catalyst comprising a catalytically effective amount of tantalum pentachloride ($TaCl_5$).

DETAILED DESCRIPTION OF THE INVENTION

The process of this invention is applicable to the reaction of an olefin (formula I) with an alkyl ester of acrylic acid (II) for preparation of a higher alkyl acrylic acid ester compound (III), as represented by the equation

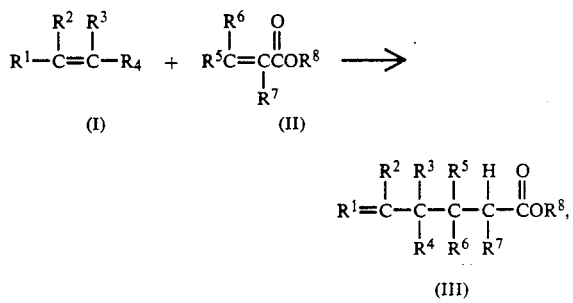

wherein $R^1$ is alkyl, $R^2$, $R^3$, $R^4$, $R^5$, $R^6$, and $R^7$ are each individually selected from the group consisting of hydrogen and of alkyl moieties, and $R^8$ represents an alkyl group.

The reactant olefins are acyclic alkenes, and suitably encompass diolefins, particularly non-conjugated diolefins. In general, the olefin reactant molecule may have from 3 to about 40 carbon atoms. Preferably, the invention is applied to a liquid phase reaction involving olefins in the carbon number range from about 6 to about 30, inclusive. In one respect, preference can be expressed for an olefin reactant carbon number in the range from about 8 to about 20, inclusive, particularly a carbon number in the range from about 14 to about 18, inclusive. The olefin molecule is suitably either branched or linear and may have either an alpha- or an internal double bond position. Olefins having a vinylidene structure have been found to be generally more reactive than olefins of a linear structure. More highly branched olefins, produced for example by oligomerization of propylene and butylene, are very suitable reactants. Linear internal olefins have generally been observed to have relatively low reactivity and to generate substantial amounts of side products.

Mixed olefin reactants are very suitable. However, as recognized in U.S. Pat. No. 4,822,911, olefins of different molecular structure may have different reactivities under certain process conditions. Linear olefins having an internal double bond position have also been observed to react more slowly than olefins of other structures and to form substantial amounts of side product.

The lower alkyl esters of acrylic acid which are employed as reactants in this invention are suitably acrylates and alkyl-substituted acrylates represented by formula II above. Mixtures of different alkyl acrylic acid esters are suitable reactants.

The $R^8$ substituent of the ester reactant molecule is preferably an alkyl group having a carbon number of up to about 30, more preferably one having from 1 to about 15 carbon atoms, and most preferably one having from 1 to about 8 carbon atoms. The $R^5$, $R^6$ and $R^7$ substituents each independently represent either a hydrogen atom or an alkyl group, preferably, a hydrogen atom or a lower, i.e., $C_1$ to $C_4$ alkyl group. If desired, the acrylate ester reactant may be suitably substituted with one or more non-hydrocarbyl substituents which do not substantially affect the intended reaction. As an example, one or more of the $R^5$, $R^6$, and $R^7$ substituents is suitably a halogen or a halogen substituted alkyl group.

Specific examples of alkyl acrylic acid ester reactants include methyl acrylate, ethyl acrylate, n-propyl acrylate isopropyl acrylate, n-butyl acrylate, isobutyl acrylate, tertiary-butyl acrylate, n-octyl acrylate, isooctyl acrylate, 2-ethylhexyl acrylate, n-tetradecyl acrylate, n-hexadecyl acrylate and methyl alpha-chloroacrylate. In one respect, alkyl acrylic acid esters having from 4 to about 8 total carbon atoms are particularly preferred ester reactants. In another respect, preference can be expressed for ester reactants in which the $R^5$, $R^6$, and $R^7$ substituents are each hydrogen. Very good results have been obtained with methyl acrylate.

Also suitable as alkyl acrylic acid ester reactants in this process are the dimers, trimers, and other oligomers of the indicated acrylic acid esters, such as, for example, trimethylolpropane triacrylate, 1,6-hexanediol diacrylate, and the like.

The relative proportions of the olefin reactant and the ester reactant are not critical to the invention. However, preference can be expressed for a molar ratio of olefin to ester reactant in the range from about 1:30 to about 10:1. A molar ratio of olefin to ester in the range from about 1:10 to about 10:1 is considered more preferred, while a ratio between about 1:4 and about 1:1 is considered of particular advantage in order to obtain good conversion to the desired product, while minimizing formation of olefin dimer side products.

For purposes of the process of this invention, the olefin reactant and the alkyl acrylic acid ester reactant are contacted, in the liquid phase, in the presence of a catalytically effective amount of tantalum pentachloride. The contact and reaction may take place in either a batch or continuous mode.

The catalyst is suitably present in solution in the reaction mixture in a catalytically effective amount, typically at least about 0.01 percent by mol (% m), based on mols of the olefin. Catalyst quantities in the range from about 0.01 to about 5% m are generally preferred, while quantities in the range from about 0.1 to about 2% m are considered most preferred. Substantially greater quantities of catalyst, e.g., up to 30% m or more, can be used if desired. As a general rule, the catalyst is soluble, at least in part, in the reaction mixture.

In addition to the reactants and catalyst, it has been found useful to add to the reaction mixture a small quantity of an antioxidant material such as hydroquinone, in order to inhibit free-radical catalyzed polymerization reactions involving the acrylate esters. The tantalum pentachloride catalyst can further be applied in combination with other ene reaction catalysts, e.g., other halide compounds. Transition metal (e.g., iron, nickel and copper) sulfate salts have shown some promise for modifying the reaction results.

The present invention relates primarily to the use of the tantalum pentachloride catalyst. In general, the process can otherwise be practiced under conditions characteristic of other ene reaction processes, although certain preferences can be expressed. Thus, the process is suitably carried out at a temperature in the range from about 0° to 300° C., while a temperature in the range from about 40° to 220° C. is considered preferred, a temperature in the range from about 60° to 150° C. is more preferred and a temperature in the range from about 80° to 120° C. is considered most preferred. Pressure is not a critical variable in the process of the invention, although it is desirable that the pressure be sufficient to maintain the olefin and ester reactants substantially in the liquid phase. Operation at pressures between about 0 and 1000 psig are very convenient, although higher pressures, e.g., 2000 psig or greater, are also suitable. If desired, the process can be carried out using a lower carbon number olefin reactant predominantly in the vapor phase under process conditions, and a liquid phase ester reactant.

The process of the invention can be practiced in the presence of a reaction solvent (e.g., benzene, toluene, hexane, carbon tetrachloride, ethylene chloride, ethyl acetate or other solvents recognized in the art for service in ene reactions). Solvents often enhance reaction rate. However, such solvents are not necessary and are inconvenient to remove from the product. Accordingly, it is generally preferred that the process mixture be substantially free of added solvents.

The contact/reaction step converts the reactants, in whole or in part, to higher alkyl acrylic acid ester adducts of the olefins. The product comprises the higher alkyl acrylic acid ester adducts of the olefins represented by formula III above, as well as other higher alkyl acrylic acid ester adduct isomers. Adducts of two or more ester molecules and one olefin molecule may also be produced, particularly when the process is practiced with excess ester reactant. Ene reactions of olefins with acrylate esters are known to produce side products including diesters, dimers, and catalyst derivatives such as chlorinated hydrocarbons (alkyl chlorides).

The present invention is, in one respect, useful for the addition of alkyl acrylic acid esters to branched olefins molecules. In this respect, the invention can be applied to the reaction of highly branched olefin mixtures such as propylene and butylene trimers, tetramers and pentamers, and other products of the oligomerization of lower olefins.

The reaction may be terminated by depletion of one or both of the reactants, or upon cooling of the reaction mixture, e.g., to a temperature of about 0° C. or less. Either during or following termination of the reaction, the product mixture is preferably treated for separation, e.g., by filtration, of catalyst and/or catalyst residues. Generally the catalyst is at least partially soluble in the reaction mixture. To extract catalyst and catalyst residues from solution, it has been found useful to wash the mixture with an aqueous acid solution, e.g., with an equal volume of a 1 to 10% w aqueous sulfuric acid solution. This extraction technique is further described in the commonly-assigned copending application, Ser. No. 07/510,311, filed Apr. 17, 1990, the disclosure of which is incorporated herein by this reference.

Separation of the higher alkyl acrylic acid ester products from unreacted olefin and/or ester starting materials can be accomplished by distillation or by other procedures known in the art for the processing of ene reaction products.

The invention is particularly useful when applied in connection with the process described in the U.S. Pat. No. 4,822,911. For purposes of that process, a mixture of higher carbon number linear olefins and ethyl- and higher alkyl-branched vinylidene olefins is contacted with one or more alkyl esters of acrylic acid in the presence of an ene reaction catalyst, to accomplish, via selective reaction of the vinylidene olefins, both a separation of vinylidene olefins from the linear olefins and a conversion of the alkyl acrylic acid esters to higher esters. The teachings of the process of U.S. Pat. No. 4,822,911 are incorporated herein by this reference.

The process of the invention is further described with reference to the following examples, which are intended to illustrate certain preferred embodiments without limiting the invention's broader scope.

Two different analytical procedures (designated a) and b)) were applied in evaluating the results of the experimental examples. Both involved GC (gas chromatography) techniques, but utilized different GC columns. Analytical technique b) is considered more suited to accuracy in quantifying the higher carbon number components of the product mixtures, particularly the olefin dimer side product.

EXAMPLE 1

A process according to the invention was carried out for the reaction of methyl acrylate with a $C_{16}$ olefin reactant having vinylidene carbon structure. For this purpose, 9.88 grams of the vinylidene olefin were contacted with methyl acrylate in a stirred 100 ml autoclave under nitrogen atmosphere. Hydroquinone was added in a quantity of 0.05 grams. Other parameters for this example together with the process results, are presented in the following tables. Relative selectivities to both the 1:1 adduct (i.e., one mol of olefin to one mol of ester) and the 1:2 adduct (i.e., one mol of olefin to two mols of ester) are reported, as well as the selectivity for production of principal side products (olefin dimer and organic chlorides). These selectivities are in percentages, relative to the total of the 1:1 adduct, the 1:2 adduct and the side products. Total conversion of the olefin is also reported.

EXAMPLE 2

Following the same general procedures of Example 1, the invention was applied to the reaction of a propylene pentamer olefin reactant (20 grams) with methyl acrylate (8.18 grams) in the presence of tantalum chloride (3.41 grams). Parameters and results are reported in the following tables.

EXAMPLES 3-5

A series of experiments according to the invention were carried out for which various olefin reactants were reacted with methyl acrylate in the presence of mixtures of tantalum chloride and another chloride compound—either cesium chloride or ethyl aluminum dichloride—known for activity in promoting ene reactions. For example 3, the olefin reactant had carbon number of 16 and a vinylidene structure. In example 4, the olefin reactant was a mixture of $C_{16}$ olefins, containing about 24% of vinylidene olefins and 76% of linear olefins greater than 90% of which were alpha olefins. For example 5, the reactant was a mixture of $C_{13}$ and $C_{14}$ olefins, which were substantially of linear carbon structure and had internal double bond position. Hydroquinone was added in a quantity of 0.05 grams. Other parameters for these examples together with the process results, are presented in the following tables.

| Example No. | Catalyst: grams | Grams olefin:MA | Reaction time (hr) | Reaction temp. (°C.) |
| --- | --- | --- | --- | --- |
| 1 | $TaCl_5$: 1.58 | 9.88:17.8 | 16 | 100 |
| 2 | $TaCl_5$: 3.41 | 20:8.18 | 16 | 150 |
| 3 | $TaCl_5$: 1.58 CsCl: 0.37 | 9.88:17.8 | 16 | 100 |
| 4 | $TaCl_5$: 3.15 CsCl: 1.48 | 19.76:15.1 | 16 | 140 |
| 5 | $TaCl_5$: 3.58 $EtAlCl_2$: 0.13 | 19:8.61 | 16 | 140 |

| Example No. | 1:1 adduct | 1:2 adduct + olefin dimer | Organic chlorides | Total conversion of olefin |
| --- | --- | --- | --- | --- |
| 1 - a) | 46.9% | 13.4% total | 39.7% | 42% |
| 2 - a) | 99% | — | — | 17.4% |
| - b) | 83.5% | 2.9% + 13.6% | — | 13% |
| 3 - a) | 82.3% | 8.5% + 0% | 9.2% | 49.8% |
| 4 - a) | 57.4% | 22.3% + 18.5% | 1.7% | 38.6% |
| 5 - a) | 8.8% | — | 91.2% | 29% |

COMPARATIVE EXPERIMENTS A-T

Although certain halide salts are known in the prior art to catalyze ene reactions between olefins and alkyl acrylic acid esters, it cannot be said that the performance of halide compounds in general as potential catalysts for the reaction of interest is at all predictable.

The following tables present the parameters and results for a number of comparative experiments, not in accordance with the invention, in which olefins were contacted with methyl acrylate ("MA") in the presence of various halide compounds and other salts. Several different olefin reactants were employed: the mixture of $C_{16}$ vinylidene and alpha-olefins as described in example 1 (designated $C_{16}$VO/AO); a $C_{16}$ vinylidene olefin reactant (designated $C_{16}$VO); and a propylene pentamer reactant (designated PP).

| Experiment | Catalyst (grams) | Olefin (grams) | MA Ester (grams) | Reaction time (hr) | Reaction temp. (°C.) |
| --- | --- | --- | --- | --- | --- |
| A | [1)]$BF_3$ (0.3) | $C_{16}$VO (9.88) | (17.8) | 16 | 100 |
| B | [2)]$Ph_3CBF_4$ (1.45) | $C_{16}$VO (9.88) | (17.8) | 16 | 100 |
| C | $AlCl_3$ (0.59) | $C_{16}$VO (9.88) | (17.8) | 16 | 100 |
| D | $FeCl_3$ (0.71) | $C_{16}$VO (9.88) | (7.58) | 16 | 100 |
| E | $Ca(BF_4)_2$/CsCl (0.94/0.37) | $C_{16}$VO (19.76) | (15.1) | 16 | 100 |
| F | [3)]$BF_3$ (1.25) | $C_{16}$VO (19.76) | (15.16) | 16 | 100 |
| G | [4)]$Al(O-nBu)_3$ (2.17) | $C_{16}$AO/VO (19.76) | (15.1) | 16 | 100 |
| H | [5)]$Ti(OMe)_4$ (1.51) | $C_{16}$AO/VO (19.76) | (15.1) | 16 | 100 |
| I | $SnCl_2$ (1.67) | $C_{16}$AO/VO (19.76) | (15.1) | 16 | 100 |

-continued

| Experiment | Catalyst (grams) | Olefin (grams) | MA Ester (grams) | Reaction time (hr) | Reaction temp. (°C.) |
|---|---|---|---|---|---|
| J | [6]Zr(O-iPr)$_4$ (3.41) | C$_{16}$AO/VO (19.76) | (15.1) | 16 | 100 |
| K | [7]BCl$_3$ (1.03) | C$_{16}$AO/VO (19.75) | (1.89) | 16 | 100 |
| L | AlF$_3$ (0.90) | C$_{16}$AO/VO (19.75) | (1.89) | 16 | 100 |
| M | [8]Al(iBu)$_3$ (0.44) | C$_{16}$AO/VO (19.75) | (1.81) | 15 | 80 |
| N | [3]BF$_3$ (1.35) | PP (20) | (8.18) | 8 | 80 |
| O | SnCl$_4$ (2.48) | PP (20) | (8.18) | 8 | 150 |
| P | AlCl$_3$ (6.53) | PP (20) | (42) | 8 | 110 |
| Q | ZnCl$_2$ (1.3) | PP (20) | (8.18) | 3 | 150 |
| R | LaCl$_3$ (2.33) | PP (20) | (42) | 8 | 80 |
| S | BaSO$_4$ (2.22) | PP (20) | (8.18) | 16 | 150 |
| T | SbCl$_5$ (2.84) | PP (20) | (8.18) | 16 | 80 |

[1] BF$_3$ in methanol (0.3 grams BF$_3$).
[2] Triphenyl carbonium tetrafluoroborate.
[3] BF$_3$-etherate (1.25 grams BF$_3$).
[4] Aluminum n-butoxide.
[5] Titanium methoxide.
[6] Zirconium isopropoxide.
[7] BCl$_3$ in hexane (1.03 grams BCl$_3$).
[8] Tri-isobutyl aluminum.

| Experiment | % Olefin conversion to 1:1 adduct | 1:2 adduct | side products | Total conversion of olefin |
|---|---|---|---|---|
| A - a | — | — | — | 0.1% |
| B - a | 92.0% | 4.1% | 3.9% | 7% |
| C - a | 68% | 27.4% | 4.6% | 84.4% |
| D - a | 25% | — | 75% | 6.4% |
| E - a | — | — | — | 0.9% |
| F - a | 92% | 8% | — | 13% |
| G - a | — | — | — | <1% |
| H - a | — | — | — | <1% |
| I - a | — | — | — | <1% |
| J - a | — | — | — | <1% |
| K - a | 78.7% | — | 21.3% | 3.1% |
| L - a | — | — | — | <1% |
| M - a | — | — | — | 0% |
| N - a | — | — | — | 0% |
| O - b | 78% | 22% | — | 12.2% |
| P - b | 94.7% | 4.6% | 0.6% | 32.2% |
| Q - a | — | — | — | <1% |
| R - a | — | — | — | 0% |
| S - b | 73.9% | 22.7% | 3.4% | 1.8% |
| T - b | 91.3% | 4.5% | 4.2% | 1% |

EXAMPLE 6 AND COMPARATIVE EXPERIMENTS U AND V

For example 6, methyl acrylate was contacted and reacted with 1-octene in an 80 ml autoclave in the presence of a mixture of tantalum pentachloride and lithium chloride (in a 1:1 molar ratio of Ta and Li). The molar ratio of olefin to methyl acrylate to pentachloride was 1:4:0.1. Hydroquinone was added (a few milligrams) as inhibitor. After an 18 hour reaction at 88° C. and under a nitrogen atmosphere (500 psig), 71 percent of the olefin had been converted with a selectivity to ester products of 82 percent.

In comparative experiment U, the procedures and conditions of example 6 were repeated, with the substitution of aluminum chloride for the tantalum pentachloride and at a temperature of 95° C. Conversion of olefin was reduced to 62 percent, and selectivity to esters was reduced to 75 percent. Comparative experiment V repeated the procedures and conditions of example 6, but omitted catalyst addition and maintained a temperature of 104° C. Less than 5% conversion of the olefin was observed.

We claim as our invention:

1. A process for the preparation of higher alkyl acrylic acid esters which comprises contacting and reacting under a temperature in the range of from about 40° C. to about 220° C. and a pressure in the range of from about 0 psig and about 1000 psig at least one olefin with at least one alkyl acrylic acid ester in the presence of a catalytically effective amount of tantalum pentachloride.

2. The process of claim 1, wherein the olefins have carbon numbers in the range from about 6 to 30, inclusive.

3. The process of claim 2, wherein the reactant alkyl acrylic acid esters have carbon numbers in the range from about 4 to about 8, inclusive.

4. The process of claim 3, wherein the reactant olefins have carbon numbers in the range from about 8 to 20, inclusive.

5. The process of claim 4, wherein olefins having carbon numbers in the range from about 14 to about 18, inclusive, are contacted and reacted with methyl acrylate.

6. The process of claim 1, wherein the contact and reaction take place in the presence of from about 0.01 to about 5 percent by mol of tantalum pentachloride.

7. The process of claim 5, wherein the contact and reaction take place in the presence of from about 0.01 to about 5 percent by mol of tantalum pentachloride.

* * * * *